US006369033B1

(12) United States Patent
Steinman et al.

(10) Patent No.: US 6,369,033 B1
(45) Date of Patent: *Apr. 9, 2002

(54) METHODS FOR TREATMENT OF MULTIPLE SCLEROSIS USING PEPTIDE ANALOGUES AT POSITION 91 OF HUMAN MYELIN BASIC PROTEIN

(75) Inventors: Lawrence Steinman, Palo Alto; Nicholas Ling, San Diego; Paul J. Conlon, Solana Beach; Amitabh Gaur, San Diego, all of CA (US)

(73) Assignees: Stanford University Medical Center, Palo Alto; Neurocrine Biosciences, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/953,937

(22) Filed: Oct. 20, 1997

Related U.S. Application Data

(63) Continuation of application No. 08/342,078, filed on Nov. 18, 1994, now abandoned.

(51) Int. Cl.[7] .................. A61K 38/10; A61K 38/17; C07K 7/08; C07K 14/47

(52) U.S. Cl. .................. 514/14; 514/21; 530/327; 530/350

(58) Field of Search ................ 530/327, 350, 530/839; 514/12, 14, 21, 903

(56) References Cited

U.S. PATENT DOCUMENTS 5,468,481 A * 11/1995 Sharma et al. ............ 530/402
5,858,980 A * 1/1999 Weiner et al. ............ 514/13

FOREIGN PATENT DOCUMENTS

| WO | 12816 | * 9/1991 |
| WO | WO 92/21367 | 12/1992 |
| WO | 8212 | * 4/1993 |
| WO | 21222 | * 10/1993 |
| WO | WO 95/08572 | 3/1995 |

OTHER PUBLICATIONS

Cover of Journal of Immunology, vol. 153, No. 4, issued Aug. 15, 1994 (date–stamped Aug. 11, 1994).*

Chou et al., "Identity of Myelin Basic Protein from Multiple Sclerosis and Human Control Brains: Discovery of a Genetic Variant," *Journal of Neurochemistry* 30: 745–750, 1978.

Einstein et al., "Suppression of Experimental Allergic Encephalomyelitis By Chemically Modified Encephalitogen," *Immunochemistry* 9: 1013–1019, 1972.

Evavold and Allen, "Separation of IL–4 Production from Th Cell Proliferation by an Altered T Cell Receptor Ligand," *Science* 252: 1308–1310, 1991.

Gautam et al., "A Polyalanine Peptide With only Five Native Myelin Basic Protein Residues Induces Autoimmune Encephalomyelitis," *J. Exp. Med.* 176: 605–609, 1992.

(List continued on next page.)

*Primary Examiner*—Jeffrey E. Russel
(74) *Attorney, Agent, or Firm*—Seed Intellectual Property Law Group PLLC

(57) ABSTRACT

Peptide analogues of human myelin basic protein containing residues 87–99 are provided. Residue 91 of the peptide analogues is altered from the L-lysine residue found in the native protein to any other amino acid. Pharmaceutical compositions of the peptide analogues are provided. In addition, the peptide analogues are administered to patients with multiple sclerosis.

10 Claims, 5 Drawing Sheets

OTHER PUBLICATIONS

Hashim et al., "Suppression and Reversal of Allergic Encephalomyelitis in Guinea Pigs with a Non–Encephalitogenic analogue of the Tryptophan Region of the Myelin Basic Protein," *Journal of Immunology* 116(1): 126–130, 1976.

Kardys and Hashim, "Experimental Allergic Encephalomyelitis in Lewis Rats: Immunoregulation of Disease By a Single Amino Acid Substitution in the Disease–Inducing Determinant," *Journal of Immunology* 127(3): 862–866, 1981.

Karin et al., "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production," *J. Exp. Med.* 180: 2227–2237, 1994.

Martin et al., "Diversity of Fine Specificity and T Cell Receptor Usage of the Human CD4[30] Cytotoxic T Cell Response Specific for the Immunodominant Myelin Basic Protein Peptide 87–106," *Journal of Immunology* 148(5): 1359–1366, 1992.

Servis et al., "Two adjacent epitopes on a synthetic dodecapeptide induce lactate dehydrogenase B–specific helper and suppressor T cells," *Proc. R. Soc. Lond. B* 228: 461–470, 1986.

Sette et al., "Analysis of lysozyme–specific immune responses by synthetic peptides. I. Characterization of antibody and T cell–mediated responses to the N–terminal peptide of hen egg–white lysozyme," *Eur. J. Immunol.* 16: 1–6, 1986.

Smilek et al., "A single amino acid change in a myelin basic protein peptide confers the capacity to prevent rather than induce experimental autoimmune encephalomyelitis," *Proc. Natl. Acad. Sci. USA* 88: 9633–9637, 1991.

Su et al., "Synthetic Myelin Basic Protein Peptide Analogs Are Specific Inhibitors of Phospholipid/Calcium–Dependent Protein Kinase (Protein Kinase C)," *Biochemical and Biophysical Research Communications* 134(1): 78–84, 1986.

Abstract 65027 from *Biol. Abstr.* 81(7): AB–701 (1985) of the article "Monoclonal antibodies to human myelin basic protein," by Chou et al., *J. Neurochem.* 46(1): 47–53, 1985.

Acha–Orbea et al., "Limited Heterogeneity of T Cell Receptors from Lymphocytes Mediating Autoimmune Encephalomyelitis Allows Specific Immune Intervention," *Cell* 54: 263–273, 1988.

Babbitt et al., "Antigenic competition at the level of peptide–Ia binding," *Proc. Natl. Acad. Sci. USA* 83: 4509–4513, 1986.

Bernard C., "Experimental Autoimmune Encephalomyelitis in Mice: Genetic Control of Susceptibility," *Journal of Immunogenetics* 3: 263–274, 1976.

Brocke et al., "In Vitro Proliferative Responses and Antibody Titers Specific to Human Acetylcholine Receptor Synthetic Peptides in Patients with Myasthenia Gravis and Relation to HLA Class II Genes," *J. Clin. Invest.* 81: 1894–1900, 1988.

Brostoff and Howell, "T Cell Receptors, Immunoregulation, and Autoimmunity," *Clinical Immunology and Immunopathology* 62(1): 1–7, 1992.

Day et al., "The Polyclonal Antibody Responses of Lewis Rats to the Synthetic Encephalitogenic Neuropeptide S55S (Residues 72–84 of Guinea Pig Myelin Basic Protein) and Its Analogs," *Journal of Neuroscience Research* 18: 214–221, 1987.

Gammon et al., "Neonatal T–cell tolerance to minimal immunogenic peptides is caused by clonal inactivation," *Nature* 319: 413–415, 1986.

Gaur et al., "Amelioration of Autoimmune Encephalomyelitis by Myelin Basic Protein Synthetic Peptide–Induced Anergy," *Science* 258: 1491–1494, 1992.

Gautam et al., "Inhibition of Experimental Autoimmune Encephalomyelitis By a Nonimmunogenic Non–Self Peptide That Binds to I–A"," *Journal of Immunology* 148(10): 3049–3054, 1992.

Hadden et al., "Thymic Hormones, Interleukins, Endotoxin and Thymomimetic Drugs in T Lymphocyte Ontogeny," in *Advances in Immunopharmacology 3*, L. Chedid et al. (Eds.), 1985, pp. 487–497.

Hashim and Day, "Synthetic Peptide Analogs to Probe the Immunological Expression of the Rat Encephalitogenic Neuropeptide," *Journal of Neuroscience Research* 18: 209–213, 1987.

Hashim, G., "Experimental Allergic Encephalomyelitis: Activation of Suppressor T Lymphocytes By a Modified Sequence of the T Effector Determinant," *Journal of Immunology* 126(2): 419–423, 1981.

Jahnke et al., "Sequence Homology Between Certain Viral Proteins and Proteins Related to Encephalomyelitis and Neuritis," *Science* 229: 282–284, 1985.

Kira et al., "Experimental Allergic Encephalomyelitis in Rabbits. A Major Encephalitogenic Determinant within Residues 1–44 of Myelin Basic Protein," *J. of Neuroimmunol.* 12(3): 183–193, 1986.

Lehninger, A., "The Amino Acid Building Blocks of Proteins," in *Biochemistry*, 2nd ed., Worth Publishers, Inc. pp. 71–75, 1975.

Martin et al., "A Myelin Basic Protein Peptide Is Recognized by Cytotoxic T Cells in the Context of Four HLA–DR Types Associated with Multiple Sclerosis," *Journal of Experimental Medicine* 173: 19–24, 1991.

Rothbard, J., "Peptides and the Cellular Immune Response," *Ann. Inst. Pasteur/Virologie* 137 E: 518–526, 1986.

Rothbard and Taylor, "A sequence pattern common to T cell epitopes," *EMBO J.* 7(1): 93–100, 1988.

Rudinger, J., "Characteristics of the amino acids as components of a peptide hormone sequence," in *Peptide Hormones*, J. A. Parsons (ed.), University Park Press, Baltimore, pp. 1–7, 1976.

Sriram et al., "Administration of Myelin Basic Protein–Coupled Spleen Cells Prevents Experimental Allergic Encephalitis," *Cellular Immunology* 75: 378–382, 1983.

Steinman et al., "Regulation of autosensitisation to encephalitogenic myelin basic protein by macrophage–associated and soluble antigen," *Nature* 265: 173–175, 1977.

Steinman et al., "Natural occurrence of thymocytes that react with myelin basic protein," *Neurology* 30(7): 755–759, 1980.

Talmadge et al., "Screening Models for Biological Response Modifiers," in *13th International Congress of Chemotherapy. Symposium, Biological Response Modifiers*; SY 64 part 203, Vienna Aug. 28–Sep. 2, 1993, pp. 203/19–203/34.

Wraith et al., "T Cell Recognition as the Target for Immune Intervention in Autoimmune Disease," *Cell 57*: 709–715, 1989.

Zamvil and Steinman, "The T Lymphocyte in Experimental Allergic Encephalomyelitis," *Annu. Rev. Immunol. 8*: 579–621, 1990.

Zamvil et al., "Encephalitogenic T Cell Clones Specific for Myelin Basic Protein," *J. Exp. Med. 162*: 2107–2124, 1985.

Zamvil et al., "T–cell clones specific for myelin basic protein induce chronic relapsing paralysis and demylination," *Nature 317*: 355–358, 1985.

Zamvil et al., "T–cell epitope of the autoantigen myelin basic protein that induces encephalomyelitis," *Nature 324*: 258–260, 1986.

Zamvil, S., "T–Cell Specificity for Class II(I–A) and the Encephalitogenic N–Terminal Epitope of the Autoantigen Myelin Basic Protein," *Journal of Immunology 139*(4): 1075–1079, 1987.

Zamvil et al., "Multiple Discrete Encephalitogenic Epitopes of the Autoantigen Myelin Basic Protein Include a Determinant for I–E Class II–Restricted T Cells," *J. Exp. Med. 168*: 1181–1186, 1988.

Carter and Rodriguez, "Immunosuppressive Treatment of Multiple Sclerosis," *Mayo Clin. Proc. 64*: 664–669, 1989.

Kuchroo et al., "A Single TCR Antagonist Peptide Inhibits Experimental Allergic Encephalomyelitis Mediated by a Diverse T Cell Repertoire," *Journal of Immunology 153*:3326–3336, 1994.

Lamont et al., "Inhibition of Experimental Autoimmune Encephalomyelitis Induction In SJL/J Mice By Using A Peptide With High Affinity For IA$^s$ Molecules," *Journal of Immunology 145*(6): 1687–1693, 1990.

Martin et al., "Immunological Aspects of Demyelinating Diseases,"*Annu. Rev. Immunol. 10*: 153–87, 1992.

Sakai et al., "Prevention of experimental encephalomyelitis with peptides that block interaction of T cells with major histocompatibility complex proteins," *Proc. Natl. Acad. Sci. USA 86*: 9470–9474, 1989.

Steinman et al., "The Epigenetics Of Multiple Sclerosis: Clues to Etiology and a Rationale for Immune Therapy," *Annu. Rev. Neurosci. 17*: 247–65, 1994.

Teitelbaum et al., "Specific inhibition of the T–cell response to myelin basic protein by the synthetic copolymer Cop 1," *Proc. Natl. Acad. Sci. USA 85*: 9724–9728, 1988.

Vogt et al., "Ligand Motifs of HLA–DRB5*0101 and DRB1*1501 Molecules Delineated from Self–Peptides," *Journal of Immunology 153*: 1665–1673, 1994.

Wraith et al., "Antigen Recognition in Autoimmune Encephalomyelitis and the Potential for Peptide–Mediated Immunotherapy," *Cell 59*: 247–255, 1989.

Wucherpfennig et al., "Structural Requirements for Binding of an Immunodominant Myelin Basic Protein Peptide to DR2 Isotypes and for Its Recognition by Human T Cell Clones," *J. Exp. Med. 179*: 279–290, 1994.

* cited by examiner

ATGGCGTCACAGAAGAGACCCTCCCAGAGGCACGGATCCAAGTACCTGGCCACAGCAAGTACCATGGACC 70

1
MetAlaSerGlnLysArgProSerGlnArgHisGlySerLysTyrLeuAlaThrAlaSerThrMetAsp 22

ATGCCAGGCATGGCTTCCTCCCAAGGCACAGAGACACGGGCATCCTTGACTCCATCGGGCGCTTCTTTGG 140

HisAlaArgHisGlyPheLeuProArgHisArgAspThrGlyIleLeuAspSerIleGlyArgPhePheGly 46

CGGTGACAGGGGTGCGCCAAAGCGGGGCTCTGGCAAGGACTCACACCACCCGGCAAGAACTGCTCACTAT 210

GlyAspArgGlyAlaProLysArgGlySerGlyLysAspSerHisHisProAlaArgThrAlaHisTyr 69

GGCTCCCTGCCCCAGAAGTCACACGGCCGGACCCAAGATGAAAACCCCGTAGTCCACTTCTTCAAGAACA 280

GlySerLeuProGlnLysSerHisGlyArgThrGlnAspGluAsnProValValHisPhePheLysAsn 92

TTGTGACGCCTCGCACACCACCCCCGTCGCAGGGAAAGGGGAGAGGACTGTCCCTGAGCAGATTTAGCTG 350

IleValThrProArgThrProProProSerGlnGlyLysGlyArgGlyLeuSerLeuSerArgPheSerTrp 116

GGGGGCCGAAGGCCAGAGACCAGGATTTGGCTACGGAGGCAGAGCGTCCGACTATAAATCGGCTCACAAG 420

GlyAlaGluGlyGlnArgProGlyPheGlyTyrGlyGlyArgAlaSerAspTyrLysSerAlaHisLys 139

GGATTCAAGGGAGTCGATGCCCAGGGCACGCTTTCCAAAATTTTTAAGCTGGGAGGAAGAGATAGTCGCT 490

GlyPheLysGlyValAspAlaGlnGlyThrLeuSerLysIlePheLysLeuGlyGlyArgAspSerArg 162

CTGGATCACCCATGGCTAGACGCTGA 516

SerGlySerProMetAlaArgArg. 170

*Fig. 1*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
    (A) LENGTH: 516 base pairs
    (B) TYPE: nucleic acid
    (C) STRANDEDNESS: single
    (D) TOPOLOGY: linear (ix) FEATURE:
    (A) NAME/KEY: CDS
    (B) LOCATION: 1..513

(xi) SEQUENCE DESCRIPTION: SEQ ID NO:1:

```
ATG GCG TCA CAG AAG AGA CCC TCC CAG AGG CAC GGA TCC AAG TAC CTG         48
Met Ala Ser Gln Lys Arg Pro Ser Gln Arg His Gly Ser Lys Tyr Leu
 -1   1               5                  10                  15

GCC ACA GCA AGT ACC ATG GAC CAT GCC AGG CAT GGC TTC CTC CCA AGG         96
Ala Thr Ala Ser Thr Met Asp His Ala Arg His Gly Phe Leu Pro Arg
                 20                  25                  30

CAC AGA GAC ACG GGC ATC CTT GAC TCC ATC GGG CGC TTC TTT GGC GGT        144
His Arg Asp Thr Gly Ile Leu Asp Ser Ile Gly Arg Phe Phe Gly Gly
             35                  40                  45

GAC AGG GGT GCG CCA AAG CGG GGC TCT GGC AAG GAC TCA CAC CAC CCG        192
Asp Arg Gly Ala Pro Lys Arg Gly Ser Gly Lys Asp Ser His His Pro
         50                  55                  60

GCA AGA ACT GCT CAC TAT GGC TCC CTG CCC CAG AAG TCA CAC GGC CGG        240
Ala Arg Thr Ala His Tyr Gly Ser Leu Pro Gln Lys Ser His Gly Arg
     65                  70                  75

ACC CAA GAT GAA AAC CCC GTA GTC CAC TTC TTC AAG AAC ATT GTG ACG        288
Thr Gln Asp Glu Asn Pro Val Val His Phe Phe Lys Asn Ile Val Thr
 80                  85                  90                  95

CCT CGC ACA CCA CCC CCG TCG CAG GGA AAG GGG AGA GGA CTG TCC CTG        336
Pro Arg Thr Pro Pro Pro Ser Gln Gly Lys Gly Arg Gly Leu Ser Leu
                100                 105                 110
```

```
AGC AGA TTT AGC TGG GGG GCC GAA GGC CAG AGA CCA GGA TTT GGC TAC         384
Ser Arg Phe Ser Trp Gly Ala Glu Gly Gln Arg Pro Gly Phe Gly Tyr
            115                 120                 125

GGA GGC AGA GCG TCC GAC TAT AAA TCG GCT CAC AAG GGA TTC AAG GGA         432
Gly Gly Arg Ala Ser Asp Tyr Lys Ser Ala His Lys Gly Phe Lys Gly
            130                 135                 140

GTC GAT GCC CAG GGC ACG CTT TCC AAA ATT TTT AAG CTG GGA GGA AGA         480
Val Asp Ala Gln Gly Thr Leu Ser Lys Ile Phe Lys Leu Gly Gly Arg
    145                 150                 155

GAT AGT CGC TCT GGA TCA CCC ATG GCT AGA CGC TGA                         516
Asp Ser Arg Ser Gly Ser Pro Met Ala Arg Arg
160                 165                 170

(2) INFORMATION FOR SEQ ID NO:2:

(i) SEQUENCE CHARACTERISTICS:
        (A) LENGTH: 171 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ser Gln Lys Arg Pro Ser Gln Arg His Gly Ser Lys Tyr Leu
 -1  1              5                  10                  15

Ala Thr Ala Ser Thr Met Asp His Ala Arg His Gly Phe Leu Pro Arg
                20                  25                  30

His Arg Asp Thr Gly Ile Leu Asp Ser Ile Gly Arg Phe Phe Gly Gly
            35                  40                  45

Asp Arg Gly Ala Pro Lys Arg Gly Ser Gly Lys Asp Ser His His Pro
        50                  55                  60

Ala Arg Thr Ala His Tyr Gly Ser Leu Pro Gln Lys Ser His Gly Arg
    65                  70                  75

Thr Gln Asp Glu Asn Pro Val Val His Phe Phe Lys Asn Ile Val Thr
 80                  85                  90                  95

Pro Arg Thr Pro Pro Ser Gln Gly Lys Gly Arg Gly Leu Ser Leu
                100                 105                 110

Ser Arg Phe Ser Trp Gly Ala Glu Gly Gln Arg Pro Gly Phe Gly Tyr
            115                 120                 125

Gly Gly Arg Ala Ser Asp Tyr Lys Ser Ala His Lys Gly Phe Lys Gly
            130                 135                 140

Val Asp Ala Gln Gly Thr Leu Ser Lys Ile Phe Lys Leu Gly Gly Arg
    145                 150                 155

Asp Ser Arg Ser Gly Ser Pro Met Ala Arg Arg
160                 165                 170
```

METHODS FOR TREATMENT OF MULTIPLE SCLEROSIS USING PEPTIDE ANALOGUES AT POSITION 91 OF HUMAN MYELIN BASIC PROTEIN

CROSS-REFERENCE TO RELATED APPLICATION

This application is a continuation of U.S. patent application Ser. No. 08/342,078, filed Nov. 18, 1994, now abandoned.

STATEMENT OF GOVERNMENT INTEREST

This invention was made with government support under contracts NS30201 and NS28759, awarded by the National Institutes of Health. The government has certain rights in this invention.

TECHNICAL FIELD

The present invention relates generally to methods for treating and preventing multiple sclerosis by using peptide analogues of human myelin basic protein.

BACKGROUND OF THE INVENTION

Multiple sclerosis (MS) is a chronic, inflammatory disease that affects approximately 250,000 individuals in the United States. Although the clinical course may be quite variable, the most common form is manifested by relapsing neurological deficits, in particular, paralysis, sensory deficits, and visual problems.

The inflammatory process occurs primarily within the white matter of the central nervous system and is mediated by T lymphocytes, B lymphocytes, and macrophages. These cells are responsible for the demyelination of axons. The characteristic lesion in MS is called the plaque due to its macroscopic appearance.

Multiple sclerosis is thought to arise from pathogenic T cells that somehow evaded mechanisms establishing self-tolerance, and attack normal tissue. T cell reactivity to myelin basic protein may be a critical component in the development of MS. The pathogenic T cells found in lesions have restricted heterogeneity of antigen receptors (TCR). The T cells isolated from plaques show rearrangement of a restricted number of V$\alpha$ and V$\beta$ gene segments. In addition, the TCRs display several dominant amino acid motifs in the third complementarity determining region (CDR), which is the major antigen contact site. All together, three CDR3 motifs have been identified in T cell clones known to recognize an epitope within amino acids 86–106 of myelin basic protein. These motifs were found in 44% of rearranged TCR sequences involving one particular V$\beta$ gene rearranged in T cells isolated from brain of two patients with MS.

A definitive treatment for MS has not been established. Historically, corticosteroids and ACTH have been used to treat MS. Basically, these drugs reduce the inflammatory response by toxicity to lymphocytes. Recovery may be hastened from acute exacerbations, but these drugs do not prevent future attacks or prevent development of additional disabilities or chronic progression of MS (Carter and Rodriguez, *Mayo Clinic Proc.* 64:664, 1989; Weiner and Hafler, *Ann. Neurol.* 23:211, 1988). In addition, the substantial side effects of steroid treatments make these drugs undesirable for long-term use.

Other toxic compounds, such as azathioprine, a purine antagonist, cyclophosphamide, and cyclosporine have been used to treat symptoms of MS. Like corticosteroid treatment, these drugs are beneficial at most for a short term and are highly toxic. Side effects include increased malignancies, leukopenias, toxic hepatitis, gastrointestinal problems, hypertension, and nephrotoxicity (Mitchell, *Cont. Clin. Neurol.* 77:231, 1993; Weiner and Hafler, supra). Antibody based therapies directed toward T cells, such as anti-CD4 antibodies, are currently under study for treatment of MS. However, these agents may cause deleterious side effects by immunocompromising the patient.

More recently, cytokines such as IFN-$\gamma$ and IFN-$\beta$ have been administered in attempts to alleviate the symptoms of MS. However, a pilot study involving IFN-$\gamma$ was terminated because 7 of 18 patients treated with this drug experienced a clinical exacerbation within one month after initiation of treatment. Moreover, there was an increase in the specific response to MBP (Weiner and Hafler, supra).

Betaseron, a modified beta interferon, has recently been approved for use in MS patients. Although Betaseron treatment showed some improvement in exacerbation rates (Paty et al., *Neurology* 43:662, 1993), there was no difference in the rate of clinical deterioration between treated and control groups (IFNB MS Study Group, *Neurology* 43:655, 1993; Paty et al., supra). Side effects were commonly observed. The most frequent of such side effects were fever (40%–58% of patients), flu-like symptoms (76% of patients), chills (46% of patients), mylagias (41% of patients), and sweating (23% of patients). In addition, injection site reactions (85%), including inflammation, pain, hypersensitivity and necrosis, were common (IFNB MS Study Group, supra; Connelly, *Annals of Pharm.* 28:610, 1994).

In view of the problems associated with existing treatments of MS, there is a compelling need for improved treatments which are more effective and are not associated with such disadvantages. The present invention exploits the use of peptide analogues which antagonize a T cell response to human myelin basic protein to effectively treat MS, while providing other related advantages.

SUMMARY OF THE INVENTION

The present invention generally provides analogues of human myelin basic protein, in which the native L-lysine residue at position 91 is altered. Within one aspect of the invention, the analogue is a peptide derived from residues 87–99 of human myelin basic protein (MBP), wherein the L-lysine residue normally found at position 91 of native peptide is altered to another amino acid. The L-lysine residue at position 91 may be altered to any other amino acid, and preferably to alanine, serine, glycine, glutamic acid, phenylalanine, arginine, asparagine, histidine, leucine or D-lysine. The alteration is preferably a non-conservative change or any D-amino acid. The alteration is also preferably one which results in reduced production of TNF-α from MBP-reactive T cells.

The present invention provides a pharmaceutical composition comprising a peptide analogue according to the embodiments set out above, in which the analogue is contained in a physiologically acceptable carrier or diluent.

The present invention also provides methods for treating multiple sclerosis by administering to a patient with MS a therapeutically effective amount of a pharmaceutical composition containing analogue as described herein. As noted above, in one aspect a peptide analogue comprises amino acid residues 87–99 of human myelin basic protein, wherein the lysine at position 91 is replaced by another amino acid.

These and other aspects will become evident upon reference to the following detailed description and attached drawings. In addition, various references are set forth below which describe in more detail certain procedures or compositions. Each of these references are incorporated herein by reference in their entirety as if each were individually noted for incorporation.

BRIEF DESCRIPTION OF THE DRAWINGS

FIG. 1 depicts DNA and predicted amino acid sequence for human myelin basic protein.

DETAILED DESCRIPTION OF THE INVENTION

Figure 2:
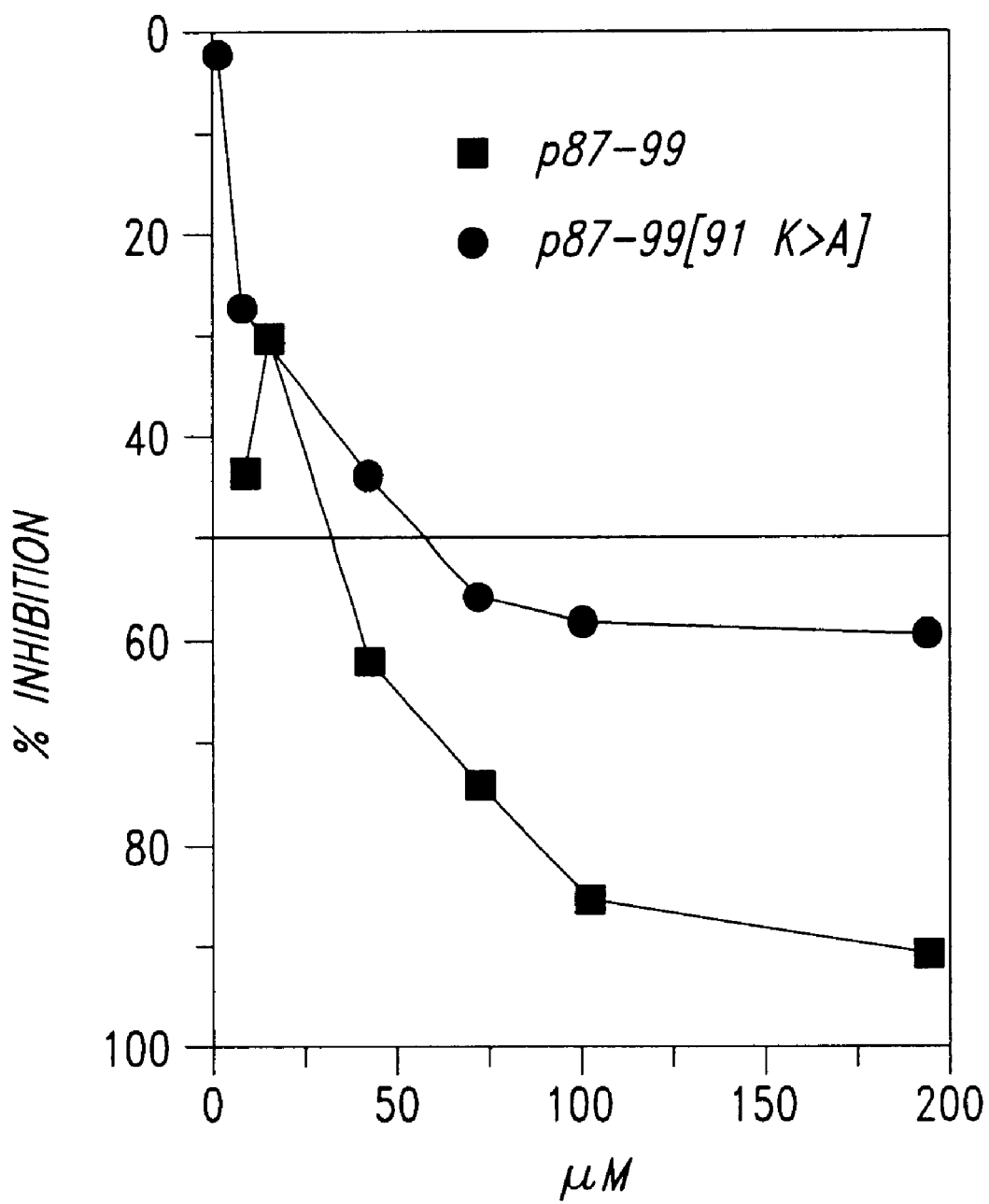
FIG. 2 is a graph demonstrating competition for MHC binding between MBP (87–99) and the alanine analogue of residue 91 (91K>A). The alanine-substituted analogue was tested at concentrations ranging from 0 to 200 μM for its ability to inhibit the binding of 10 μM biotin-labeled MBP (87–99). The data are presented as the percentage of inhibition of mean relative binding. Fifty percent inhibition establishes the $IC_{50}$ value.

Prior to setting forth the invention, it may be helpful to an understanding thereof to set forth definitions of certain terms that will be used hereinafter.

"Human myelin basic protein" ("MBP") refers to a protein found in the cytoplasm of human oligodendroglial cells. The nucleotide sequence and predicted amino acid sequence of human MBP are presented in FIG. 1 (SEQ. ID Nos. 1 and 2). Although not depicted in FIG. 1, different molecular forms of human myelin basic protein generated by differential splicing or post-translational modification are also within the scope of this invention.

"Peptide analogues" of myelin basic protein are derived from residues 87–99 of MBP and contain one difference in amino acid sequence between the analogue and native human myelin basic protein, which is a difference at residue 91. Unless otherwise indicated, a named amino acid refers to the L-form. An L-amino acid from the native peptide may be altered to any other one of the 20 L-amino acids commonly found in proteins, any one of the corresponding D-amino acids, rare amino acids, such as 4-hydroxyproline, and hydroxylysine, or a non-protein amino acid, such as α-alanine and homoserine. Also included with the scope of the present invention are amino acids which have been altered by chemical means such as methylation (e.g., α-methylvaline), amidation of the C-terminal amino acid by an alkylamine such as ethylamine, ethanolamine, and ethylene diamine, and acylation or methylation of an amino acid side chain function (e.g., acylation of the epsilon amino group of lysine).

"Residue 91," also called "position 91," refers to amino acid 91 of human myelin basic protein (see FIG. 1; SEQ. ID No. 2) or the amino acid at the comparative position for a peptide derived from MBP. The numbering system used relates to the amino acid position within the native protein, regardless of the length of the peptide or its position within that peptide.

Peptide Analogues of Myelin Basic Protein

As noted above, the present invention provides peptide analogues of myclin basic protein in which the naturally occurring L-lysine at position 91 is altered to another amino acid. The peptide analogues are derived from residues 87–99 of MBP. Residue 91, which is L-lysine in the native protein, is the key residue. Within this invention, analogues have an amino acid other than L-lysine at position 91. As noted above, any amino acid alteration at position 91 is within the scope of this invention. Preferred peptide analogues include alteration of L-lysine to any one of the following amino acids: D-lysine, alanine, glycine, glutamic acid, phenylalanine, arginine, asparagine, histidine, leucine or serine. These amino acids include both conservative (similar charge, polarity, hydrophobicity, and bulkiness) and non-conservative amino acids. Although typically one might expect that only non-conservative amino acid alterations would provide a therapeutic effect, unexpectedly even conservative changes (e.g., arginine) greatly affect the function of the peptide analogue as compared to the native peptide. Such diversity of substitution is further illustrated by the fact that the preferred amino acids noted above are hydrophobic and hydrophilic, charged and uncharged, polar and non-polar.

Peptide analogues may be synthesized by standard chemistry techniques, including synthesis by automated procedure. In general, peptide analogues are prepared by solid-phase peptide synthesis methodology which involves coupling each protected amino acid residue to a resin support, preferably a 4-methyl-benzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminus. Side-chain functional groups are protected as follows: benzyl for serine, threonine, glutamic acid, and aspartic acid; tosyl for histidine and arginine; 2-chlorobenzyloxycarbonyl for lysine and 2,6-dichlorobenzyl for tyrosine. Following coupling, the t-butyloxycarbonyl protecting group on the alpha amino function of the added amino acid is removed by treatment with trifluoroacetic acid followed by neutralization with di-isopropyl-ethylamine. The next protected residue is then coupled onto the free amino group, propagating the peptide chain. After the last residue has been attached, the protected peptide-resin is treated with hydrogen fluoride to cleave the peptide from the resin, as well as deprotect the side chain functional groups. Crude product can be further purified by gel filtration, HPLC, partition chromatography, or ion-exchange chromatography.

Peptide analogues within the present invention should (a) compete for the binding of MBP (87–99) to MHC; (b) not cause proliferation of an MBP (87–99)-reactive T cell line; and (c) inhibit induction of EAE (experimental allergic encephalomyelitis) by MBP (87–99) in rodents.

Thus, candidate peptide analogues may be screened for their ability to treat MS by (1) an assay measuring competitive binding to MHC, (2) an assay measuring a T cell proliferation, and (3) an assay assessing inhibition of EAE induction. Those analogues that inhibit binding of the native peptides, do not stimulate proliferation of MBP-reactive cell lines, and inhibit the development of EAE by native peptide, are useful therapeutics. Although not essential, a further safety assay may be performed to demonstrate that the analogue does not itself induce EAE.

Binding of peptides to MHC molecules may be assayed on whole cells. Briefly, Lewis rat spleen cells are cultured for 3 hours to allow adherent cells to stick to polystyrene petri dishes. Non-adherent cells arc removed. Adherent cells, which contain cells expressing MHC class II molecules, are collected by scraping the dishes. The binding of peptide analogues to cells is measured by a fluorescence assay. In this assay, splenic adherent cells are mixed with different concentrations of peptide analogues and incubated for 1 hour at 37° in a $CO_2$ incubator. Following incubation, biotin-labeled MBP (87–99) is added to the culture wells. The cells are incubated for another hour and then washed three times in medium. Phycoerythrin-conjugated or fluorescein-conjugated streptavidin is added along with a fluorochrome-labeled OX-6 or OX-17 monoclonal antibody, which reacts with rat MHC Class II I-A and I-E, respectively. The cells are washed twice before analysis by flow cytometry. Fluorescence intensity is calculated by subtracting the fluorescence value obtained from cells stained with phycoerythrin-streptavidin alone (control staining) from the fluorescence value obtained from biotin-labeled MBP (87–99) plus phycoerythrin-streptavidin (experimental staining). Staining without analogue establishes a 100% value. Percent inhibition is calculated for each analogue and expressed as $IC_{50}$ values. A peptide analogue with an $IC_{50}$ value of less than 100 $\mu$M is suitable for further screenings.

Candidate peptide analogues are further tested for their property of causing or inhibiting proliferation of T cell lines. Two different assays may be used as alternatives. The first measures the ability of the analogue to cause proliferation of T cells in a direct fashion. The second measures the ability of the peptide analogue to inhibit proliferation of T cells induced by native MBP (87–99) peptide.

In the direct proliferation assay, MBP (87–99) reactive T cell lines may be used as target cells. T cell lines are established from lymph nodes taken from rats injected with MBP (87–99). Lymph node cells are isolated and cultured for 5 to 8 days with MBP (87–99) and IL-2 as a source of T cell growth factors. Viable cells are recovered and a second round of stimulation is performed with MBP (87–99) and irradiated splenocytes as a source of growth factors. After 5 to 6 passages in this manner, the proliferative potential of the cell lines are determined. MBP-reactive lines are used in the proliferation assay. In this assay, T cell lines are cultured for three days with various concentrations of peptide analogues and irradiated, autologous splenocytes. After three days, 0.5–1.0 $\mu$Ci of [$^3$H]-thymidine is added for 12–16 hours. Cultures are harvested and incorporated counts determined. Mean CPM and standard error of the mean are calculated from triplicate cultures.

As an alternative to the use of T cell lines as described above, draining lymph node cells from Lewis rats immunized with MBP (87–99) may be used. Preferably, this assay is used in combination with the proliferation assay using T cell lines. Briefly, Lewis rats are injected subcutaneously with MBP (87–99) peptide in complete Freund's adjuvant. Nine to ten days later, draining lymph node cells are isolated and single-cell suspensions are prepared. Lymph node cells are incubated with various concentrations of peptide analogues for three days in a humidified air chamber containing 6.5% $CO_2$. After incubation, the cultures are pulsed with 1–2 $\mu$Ci of [$^3$H]-thymidine for 12–18 hours. Cultures are harvested on fiberglass filters and counted in a scintillation counter. Mean CPM and the standard error of the mean are calculated from data determined in triplicate cultures. Peptide analogues yielding results that are more than three standard deviations of the mean response with a comparable concentration of MBP (87–99) are considered non-stimulatory. Peptide analogues which do not stimulate proliferation at concentrations of less than or equal to 50 $\mu$M are suitable for further screenings.

The second or alternative assay is a competition assay for T cell proliferation. In this assay, antigen presenting spleen cells are first irradiated and then incubated with native MBP (87–99) peptide for 2–4 hours. These cells are then washed and further cultured with T cells reactive to MBP (87–99). Various concentrations of candidate peptide analogues are included in cultures for an additional 3 days. Following this incubation period, each culture is pulsed with 1 $\mu$Ci of [$^3$H]-thymidine for an additional 12–18 hours. Cultures are then harvested on fiberglass filters and counted as above. Mean CPM and standard error of the mean are calculated from data determined in triplicate cultures. Peptide analogues which inhibit proliferation to approximately 25% at a concentration of 50 $\mu$M or greater are suitable for further screening.

Candidate peptides that compete for binding of MBP (87–99) to MHC and do not cause direct proliferation of T cell line or can inhibit proliferation by MBP (87–99), are further tested for their ability to inhibit the induction of EAE by MBP (87–99). Briefly, 500 $\mu$g of MBP (87–99) is injected as an emulsion in complete Freund's adjuvant supplemented with heat killed *Mycobacterium tuberculosis* (H37Ra). Rats are injected subcutaneously at the base of the tail with 200 $\mu$l of the emulsion. Rats are divided into two groups. Approximately 2 days prior to disease induction (usually 10 days following injection of MBP (87–99)) rats are injected intraperitoneally either with PBS or peptide analogues in PBS. Animals are monitored for clinical signs on a daily basis by an observer blind to the treatment protocol. EAE is scored on a scale of 0–3: 0, clinically normal; 1, flaccid tail paralysis; 2, hind limb paralysis; 3, front and hind limbs affected. Peptide analogues injected at 5 mg/kg or less (approximately 1 mg per rat) are considered to inhibit the development of EAE if there is a 50% reduction in the mean cumulative score over seven days following onset of disease symptoms in the control group.

In addition, as a safety measure, but not essential to this invention, suitable peptide analogues may be tested for direct induction of EAE. As described in detail in Example 2, various amounts of peptide analogues are injected at the base of the tail of rats, and the rats examined daily for signs of EAE. A peptide analogue which is not considered to cause EAE has a mean cumulative score of less than or equal to 1 over seven days when 1 mg (5 mg/kg) in complete Freund's adjuvant is injected.

Treatment and Prevention of Multiple Sclerosis

As noted above, the present invention provides methods for treating and preventing multiple sclerosis by administering to the patient a therapeutically effective amount of a peptide analogue of human myelin basic protein as described herein. Patients suitable for such treatment may be identified by criteria establishing a diagnosis of clinically definite MS as defined by the workshop on the diagnosis of MS (Poser et al., *Ann. Neurol.* 13:227, 1983). Briefly, an individual with clinically definite MS has had two attacks and clinical evidence of either two lesions or clinical evidence of one lesion and paraclinical evidence of another, separate lesion. Definite MS may also be diagnosed by evidence of two attacks and oligoclonal bands of IgG in cerebrospinal fluid or by combination of an attack, clinical evidence of two lesions and oligoclonal band of IgG in cerebrospinal fluid. Slightly lower criteria are used for a diagnosis of clinically probable MS.

Effective treatment of multiple sclerosis may be examined in several different ways. Satisfying any of the following criteria evidences effective treatment. Three main criteria are used: EDSS (extended disability status scale), appearance of exacerbations or MRI (magnetic resonance imaging).

The EDSS is a means to grade clinical impairment due to MS (Kurtzke, *Neurology* 33:1444, 1983). Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to MS). A decrease of one full step defines an effective treatment in the context of the present invention (Kurtzke, *Ann.Neurol.* 36:573–79,1994).

Exacerbations are defined as the appearance of a new symptom that is attributable to MS and accompanied by an appropriate new neurologic abnormality (IFNB MS Study Group, supra). In addition, the exacerbation must last at least 24 hours and be preceded by stability or improvement for at least 30 days. Briefly, patients are given a standard neurological examination by clinicians. Exacerbations are either mild, moderate, or severe according to changes in a Neurological Rating Scale (Sipe et al., *Neurology* 34:1368, 1984). An annual exacerbation rate and proportion of exacerbation-free patients are determined. Therapy is deemed to be effective if there is a statistically significant difference in the rate or proportion of exacerbation-free patients between the treated group and the placebo group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group.

MRI can be used to measure active lesions using gadolinium-DTPA-enhanced imaging (McDonald et al. *Ann. Neurol.* 36:14, 1994) or the location and extent of lesions using $T_2$-weighted techniques. Briefly, baseline MRIs are obtained. The same imaging plane and patient position are used for each subsequent study. Positioning and imaging sequences are chosen to maximize lesion detection and facilitate lesion tracing. The same positioning and imaging sequences are used on subsequent studies. The presence, location and extent of MS lesions are determined by radiologists. Areas of lesions are outlined and summed slice by slice for total lesion area. Three analyses may be done: evidence of new lesions, rate of appearance of active lesions, percentage change in lesion area (Paty et al., *Neurology* 43:665, 1993). Improvement due to therapy is established when there is a statistically significant improvement in an individual patient compared to baseline or in a treated group versus a placebo group.

Candidate patients for prevention may be identified by the presence of genetic factors. For example, a majority of MS patients have HLA-type DR2a and DR2b. The MS patients having genetic dispositions to MS who are suitable for treatment fall within two groups. First are patients with early disease of the relapsing remitting type. Entry criteria would include disease duration of more than one year, EDSS score of 1.0 to 3.5, exacerbation rate of more than 0.5 per year, and free of clinical exacerbations for 2 months prior to study. The second group would include people with disease progression greater than 1.0 EDSS unit/year over the past two years.

Efficacy of the peptide analogue in the context of prevention is judged based on the following criteria: frequency of MBP reactive T cells determined by limiting dilution, proliferation response of MBP reactive T cell lines and clones, cytokine profiles of T cell lines and clones to MBP established from patients. Efficacy is established by decrease in frequency of reactive cells, a reduction in thymidine incorporation with altered peptide compared to native, and a reduction in TNF and IFN-α. Clinical measurements include the relapse rate in one and two year intervals, and a change in EDSS, including time to progression from baseline of 1.0 unit on the EDSS which persists for six months. On a Kaplan-Meier curve, a delay in sustained progression of disability shows efficacy. Other criteria include a change in area and volume of T2 images on MRI, and the number and volume of lesions determined by gadolinium enhanced images.

Peptide analogues of the present invention may be administered either alone, or as a pharmaceutical composition. Briefly, pharmaceutical compositions of the present invention may comprise one or more of the peptide analogues described herein, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g., aluminum hydroxide) and preservatives. In addition, pharmaceutical compositions of the present invention may also contain one or more additional active ingredients, such as, for example, cytokines like β-interferon.

Compositions of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulated as a lyophilizate, utilizing appropriate excipients which provide stability as a lyophilizate, and subsequent to rehydration.

Pharmaceutical compositions of the present invention may be administered in a maimer appropriate to the disease to be treated (or prevented). The quantity and frequency of administration will be determined by such factors as the condition of the patient, and the type and severity of the patient's disease. Within particularly preferred embodiments of the invention, the peptide analogue or pharmaceutical compositions described herein may be administered at a dosage ranging from 5 to 50 mg/kg, although appropriate dosages may be determined by clinical trials. Dosages of peptide analogue will be approximately 5–50 mg/kg, but are determined more accurately following trials. Patients may be monitored for therapeutic effectiveness by MRI, EDSS, and signs of clinical exacerbation, as described above.

The following examples are offered by way of illustration and not by way of limitation.

EXAMPLE 1

Peptide Synthesis

The peptides were synthesized by solid phase methodology on a peptide synthesizer (Beckman model 990). Peptides with an amidated carboxyl-terminus were prepared with a p-methylbenzhydrylamine resin (MBHA resin); for peptides with a free carboxyl-terminus, a Merrifield resin coupled with the appropriately protected amino acid was used. Both resins were obtained from Bachem Fine Chemicals (Torrance, Calif.). Derivatized amino acids (Bachem Fine Chemicals) used in the synthesis were of the L-configuration unless specified otherwise, and the N-alpha-amino function protected exclusively with the t-butyloxycarbonyl group. Side-chain functional groups were protected as follows: benzyl for serine, threonine, glutamic acid, and aspartic acid; tosyl for histidine and arginine; 2-chlorobenzyloxycarbonyl for lysine and 2,6-dichlorobenzyl for tyrosine. Coupling of the carboxyl-terminal amino acid to the MBHA resin was carried out with dicyclohexylcarbodiimide and the subsequent amino acids were coupled with dicyclohexylcarbodiimide according to Ling et al. (*Proc. Natl. Acad. Sci. USA* 81:4302, 1984). After the last amino acid was incorporated, the t-butyloxycarbonyl protecting group was removed and the peptide-resin conjugate treated with a mixture of 14 ml hydrofluoric acid (HF), 1.4 ml anisole, and 0.28 ml methylethyl sulfide per gram of resin conjugate at −20° C. for 0.5 hr and at 0° C. for 0.5 hr. HF was removed in vacuum at 0° C., and the resulting peptide and resin mixture was washed twice with diethyl ether and twice with chloroform and diethyl ether alternately. The peptide was extracted five times with 2 M acetic acid, and the extract lyophilized. The lyophilized product was first purified on a column of Sephadex G-25 fine (Pharmacia-LKB, Piscataway, N.J.) developed in 30% acetic acid to remove the truncated fragments and inorganic salts (Ling et al., 1984). Next, peptides were further purified by CM-32 carboxymethylcellulose cation-exchange chromatography (Ling et al., 1984). Final purification was achieved by partition chromatography on Sephadex G-25 fine (Ling et al., 1984). The synthetic product was characterized by amino acid analysis, mass spectrometric analysis, and reversed-phase HPLC.

EXAMPLE 2

Immunizations and EAE Induction

MBP peptides and analogues were dissolved in phosphate-buffered saline (PBS) and emulsified with an equal volume of incomplete Freund's adjuvant supplemented with 4 mg/ml heat-killed *Mycobacterium tuberculosis* H37Ra in oil (Difco Laboratories, Inc., Detroit, Mich.). Rats were immunized subcutaneously in the hind foot pads with 0.1 ml of the emulsion and were monitored for clinical signs daily by an observer blind to the treatment protocol. For intravenous injections MBP peptides and analogues were dissolved in normal saline. EAE was scored as follows: 0, clinically normal; 1, flaccid tail; 2, hind limb paralysis; 3, front and hind limb paralysis.

EXAMPLE 3

Long-term T Cell Lines

Antigen specific long-term T cell lines were derived using the method developed by Ben-Nun et al. (*Eur. J. Immunol.* 11:195, 1981). Lewis rats were injected as described above. Nine to ten days later draining lymph node cells were cultured ($10^7$/ml) for 72 hours in stimulation medium together with 10–20 μM of the injected peptide. The cells were then collected, washed, and cultured in resting medium. Resting medium was identical to the stimulation medium without autologous serum and with the addition of 10% fetal bovine serum (Gibco) and 12.5% supernatant of Con A-stimulated splenocytes as a source of T cell growth factors. Con A supernatant was prepared as described elsewhere (Ben-Nun et al., *Eur. J. Immunol.* 11:195, 1981). After an additional 5 to 8 days, cells were collected and either tested for antigen-specific proliferation or cultured for additional cycles.

EXAMPLE 4

MHC Binding Assay

The ability of MBP peptides and peptide analogues to bind MHC was measured. An assay which characterizes the binding of peptides to MHC molecules on antigen presenting cells (APC) was employed (Mozes et al., *EMBO J.* 8:4049, 1989; Gautam et al., *PNAS* 91:767, 1994). Spleen cells were cultured in Dulbecco's modified Eagle's medium supplemented with 10% fetal bovine serum (Hyclone Laboratories, Logan, Utah) in standard polystyrene petri dishes (100×15 mm) in a 37° C. incubator containing 6.5% $CO_2$ for 3 hours. Thereafter, non-adherent cells were removed, and the plates were washed three times with PBS. Adherent cells were collected using a cell scraper. The binding of MBP (87–99) analogues was measured using a fluorescence assay. Briefly, $5 \times 10^5$ splenic adherent cells in staining buffer (PBS containing 0.1% bovine serum albumin) were mixed with different concentrations ranging from 0–400 μM of MBP (87–99) analogues in individual wells of U-shape 96-well microculture plates and incubated for 1 hr at 37° C. in a 6.5% $CO_2$ incubator. Following incubation, 10 μM of biotin-labeled MBP (87–99) was added to culture wells for 1 h. Cells were washed three times with the staining buffer. Phycoerythrin-conjugated or fluoroscein-conjugated streptavidin (Becton Dickinson, San Jose, Calif.) was added as a second step reagent (1 μg/well) along with 1 μg/well of fluorochrome-labeled OX-6 or OX-17 monoclonal antibody (Pharmingen, San Diego, Calif.), which reacts with rat MHC class II I-A or I-E, respectively. The cells were washed twice before cytofluorographic analysis on a FACScan (Becton Dickinson). Fluorescence intensity for each sample was calculated by subtracting the fluorescence obtained from OX positive cells stained with phycoerythrin-streptavidin alone (control staining) from the fluorescence obtained from OX positive cells stained with biotin-labeled MBP (87–99) plus phycoerythrin-streptavidin. Percent inhibition was calculated for each analogue and expressed as $IC_{50}$ values.

As seen in FIG. 2, the native peptide effectively competed with itself for binding to APC ($IC_{50}$=14 $\mu$M). The alanine-substitution analogue (91K>A), competed nearly as effectively ($IC_{50}$=21 $\mu$M). These results indicate that the amino acid at position 91 can be changed without reducing ability of the analogue to be presented to T cells.

EXAMPLE 5

Antigen-specific Lymph Node Cell Proliferation Assay

Female Lewis rats, approximately six weeks old, were purchased from Harlan Sprague, Indianapolis, Ind. MBP peptides were dissolved in phosphate-buffered saline (PBS) and emulsified with an equal volume of complete Freund's adjuvant (Difco Laboratories, Inc., Detroit, Mich.) supplemented with 4 mg/ml of heat-killed *Myobacterium tuberculosis* H37Ra in oil (Difco). Rats were immunized subcutaneously in the base of the tail with 0.1 ml containing 100 $\mu$g of the peptide in the emulsion. Nine to ten days following immunization, rats were sacrificed, their draining lymph node removed and a single cell suspension made. Cells were resuspended to $5\times10^6$ cells per ml in stimulation medium containing Dulbecco's modified Eagle's medium (Gibco BRL, Gaithersburg, Md.) supplemented with 2 mercaptoethanol ($5\times10^{-5}$ M), L-glutamine (2 mM), sodium pyruvate (1 mM), penicillin (100 $\mu$g/ml), streptomycin (100 $\mu$g/ml), and 1% normal rat serum.

For the assay, 100 $\mu$l of the lymph node suspension was added to 96-well flat-bottom wells in the presence of an equal volume of medium containing 10 $\mu$M of various peptides (including: motilin as a negative control; MBP87–99; medium only, or alanine or D-amino acid substituted at position 91). Cultures were then incubated at 37° C. in humidified air containing 7.5% $CO_2$. After 3 days of incubation, 1.0 $\mu$Ci of tritiated thymidine (20 Ci/mM; New England Nuclear) was added to each well and the plates reincubated for an additional 12–16 hours. The plates were then harvested with a Matrix filtermate harvester (Packard) and counted using an Automatic Direct Beta Counter (Packard). Mean cpm and the standard error of the mean were calculated from triplicate wells.

Figure 4:
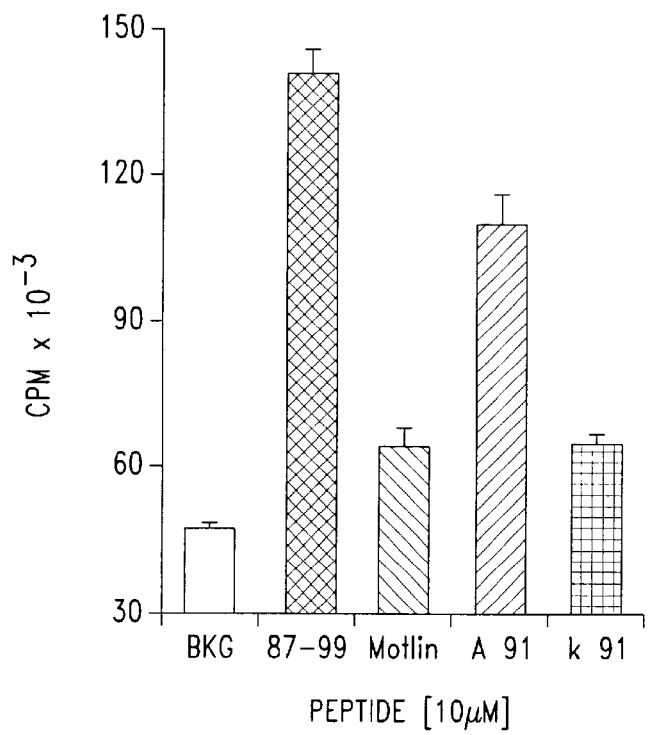
FIG. 4 is a graph displaying the proliferative response of MBP-reactive lymph node cells to position 91-substituted analogues. Two different substitutions were tested. The proliferative response of lymph node cells to 10 μM of MBP (87–99), motilin, A91 or K91 was determined. Proliferation is shown as counts per minute. BKG, no peptide added; 87–99, MBP (87–99); motilin, an unrelated peptide; A91, peptide analogue with alanine at position 91; K91, peptide analogue with D-lysine at position 91.

As seen in FIG. 4, lymph node cells (LNC) reactive to MBP (87–99) were effectively stimulated with the immunizing peptide. LNC failed to respond as well to an unrelated peptide, motilin, to media alone or the peptide analogues (91K>A) and 91K>k).

EXAMPLE 6

Antiaen-specific T Cell Line Proliferation Assays

For this antigen-specific proliferation assay, T cell lines as established in Example 3 were used. Cells were plated at a concentration of $2\times10^4$ cells/well with $10^6$ irradiated (2500 rad) splenocytes as accessory cells together with different concentrations of antigen, and incubated for three days at 37° C. Each well was pulsed with 2 $\mu$Ci of [$^3$H]-thymidine (specific activity 10 Ci/mmol) for the final 12 to 16 hours. Cultures were harvested on fiberglass filters and the proliferative response expressed as CPM±SD or as stimulation index (SI) (mean CPM from test cultures divided by mean CPM from control cultures).

Figure 3:
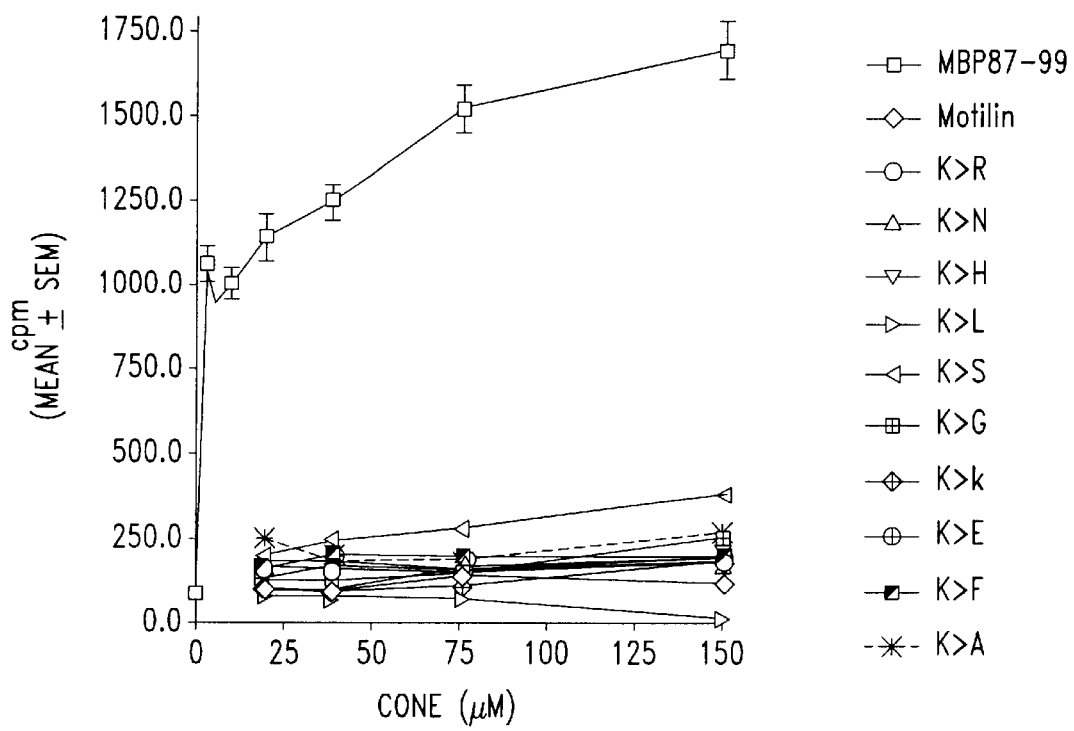
FIG. 3 is a graph displaying the proliferative response of the T cell line NBI to position 91-substituted analogues. Ten different substitutions were tested. The proliferative response of NBI in response to concentrations of analogues ranging from 0 to 150 μM was determined. Proliferation is shown as counts per minute. Standard errors of the mean were less than ±10%. MBP 87–99; peptides from human myelin basic protein containing residues 87 to 99; K, lysine; R, arginine; N, asparagine; H, histidine; L, leucine; S, serine; G, glycine; k, D-lysine; E, glutamic acid; F, phenylalanine; and A, alanine.

As seen in FIG. 3, the MBP specific rat T cell line responds to the native peptide; MBP (87–99). An irrelevant peptide motilin (MOT) does not stimulate proliferation at any dose. Ten different substitutions of position 91 were synthesized and tested in this assay. All ten peptide analogues failed to stimulate proliferation of the rat T cell line at doses ranging from 20–120 $\mu$M. Thus, for proliferation, no substitution at position 91 is tolerated.

EXAMPLE 7

Antagonism of T Cell Proliferation Assay

Figure 5:
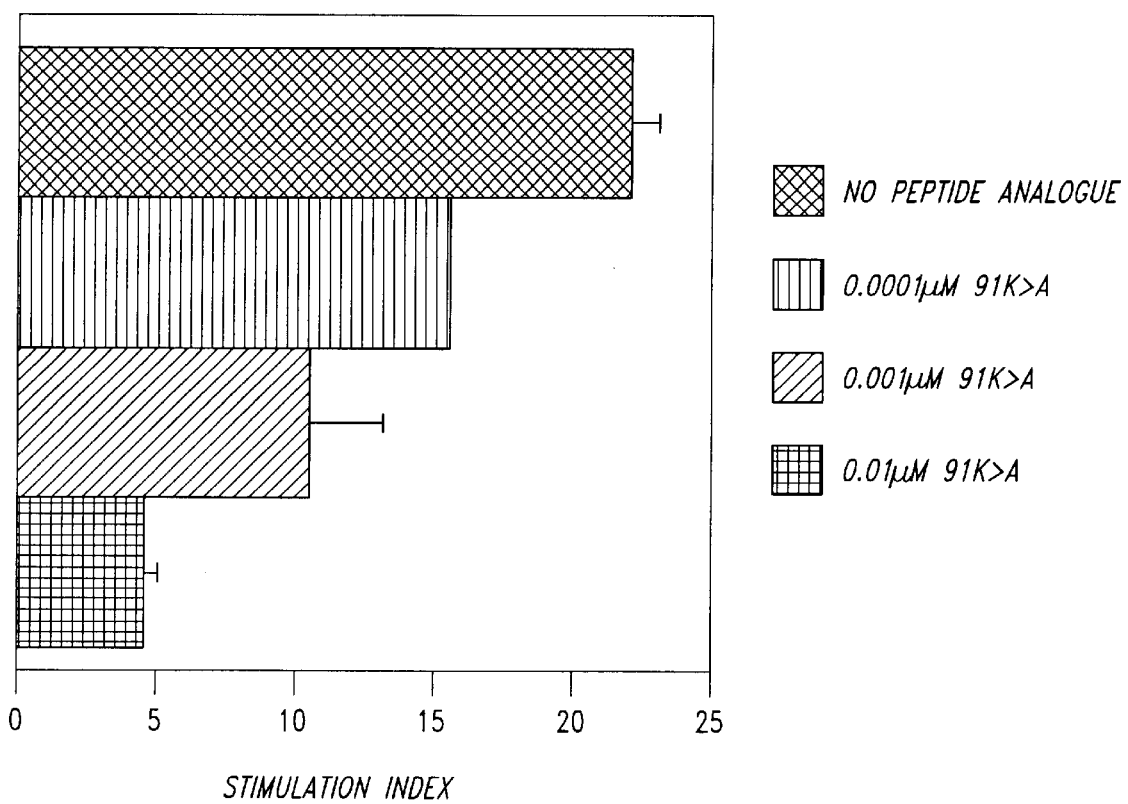
FIG. 5 is a graph illustrating the ability of alanine-substituted analogues to antagonize T cells. The proliferative response of the T cell line, L87–99, to 2.2 μM MBP (87–99) in the presence of 0.001–0.01 μM of the peptide analogue (91K>A) is shown. Results are shown as stimulation index ±SE.

T cell antagonism was detected in a prepulsed proliferation assay as described by De Magistris et al. (*Cell* 58:625, 1992) with minor modifications. Antigen presenting spleen cells were $\gamma$-irradiated (3000 rad) and incubated at a concentration of $10^7$ cells/well with 0.2 $\mu$M of the native peptide in stimulation medium in 10 ml tissue culture plates for 2.5 hours at 37° C. in a humidified air chamber containing 6.5% $CO_2$. Spleen cells were then washed and re-cultured at a concentration of $5\times10^5$ cells/well in U-shape 96-well microculture plates together with $5\times10^4$ resting anti MBP (87–99) T cell line L87–99. Various concentrations of analogues, ranging from $10^{-4}$ $\mu$M to $10^{-2}$ $\mu$M, were added for an additional 60 hours. Each well was pulsed with 1 $\mu$Ci of [$^3$H]-thymidine (specific activity 10 Ci/mmol) for the final 18 hours. The cultures were then harvested on fiberglass filters and the proliferative response expressed as CPM±SD or as stimulation index (mean CPM from test cultures divided by mean CPM from control cultures). The analogue (91K>A) was able to effectively antagonize the response of L87–99 to native peptide at all concentrations (FIG. 5). Greater than 85% inhibition was achieved at 0.01 $\mu$M of (91K>A).

EXAMPLE 8

Reversal of EAE

Figure 6:
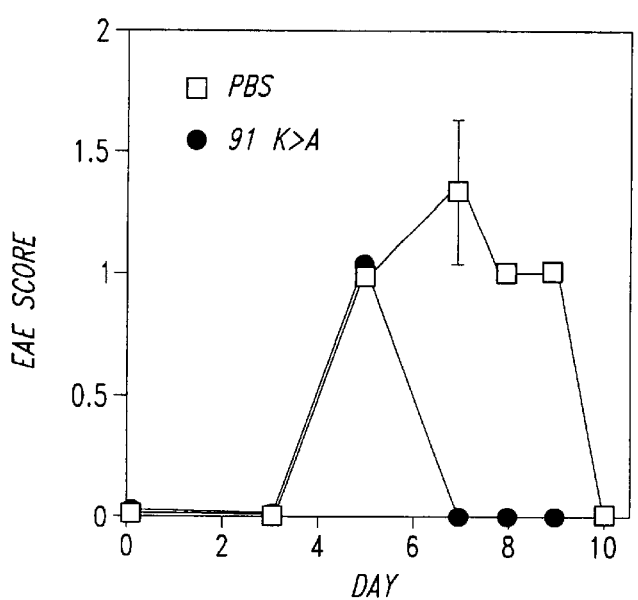
FIG. 6 is a graph depicting the reversal of EAE by soluble peptide therapy. Rats were injected with $10^7$ L87–99 cells, a procedure which induces EAE by adoptive transfer. Five days later, when clinical disease was apparent, rats were randomly distributed into three groups of six rats each. These groups were injected intraperitoneally with 2 mg/ml of either MBP (87–99) (91K>A) (-●-), or PBS (-□-). EAE was graded daily and is presented as a mean score ±SE.

Rats were given $10^7$ L87–99 T cells. All rats developed hind limb paralysis within 5 days. These paralyzed rats were then given a single injection (2 mg/ml) of soluble analogue (91K>A) or PBS. All rats receiving PBS continued to show hind limb paralysis for the following 4 days (FIG. 6, -□-). In contrast, six out of six rats treated with analogue (91K>A) went into complete remission within 36 hr without further signs of paralysis (p<0.015) (FIG. 4, -●-).

EXAMPLE 9

Induction of EAE by Peptide Analogues

The ability of peptide analogues to cause EAE is assessed in vivo. Rats were injected with MBP (87–99) or (91K>A) peptide analogue as described in Example 2. Animals were monitored daily for evidence of EAE. Rats receiving MBP (87–99) had 100% incidence (18/18 rats) of EAE with a mean maximum clinical score of 2.4±0.2. In contrast, 0/12 rats receiving the peptide analogue (91k>A) had EAE. Therefore, this peptide analogue does not induce EAE.

EXAMPLE 10

Prevention of EAE by Peptide Analogues

The ability of peptide analogues to prevent EAE when co-injected with EAE-inducing MBP (87–99) peptide was examined. MBP (87–99) was injected alone or with the peptide analogue (91K>A) in complete Freund's adjuvant at a 1:1 molar ratio. Incidence of EAE, and mean maximum clinical score data were collected.

| | Immunizing Peptides | | Peptide 1/ Peptide 2 Ratio | EAE | |
|---|---|---|---|---|---|
| Group | Peptide 1 | Peptide 2 | | Incidence | Mean Maximum Clinical Score |
| 1 | MBP(87–99) | None | | 18/18 | 2.4 ± 0.2 |
| 2 | MBP(87–99) [91K>A] | None | | 0/12 | 0 |
| 3 | MBP(87–99) | MBP(87–99) | 1:1 | 6/6 | 3 ± 0 |
| 4 | MBP(87–99) | MBP(87–99) [91K>A] | 1:1 | 0/12 | 0 |
| 5 | MBP(68–88) | None | | 6/6 | 3 ± 0 |
| 6 | MBP(68–88) | MBP(87–99) [91K>A] | 1:1 | 6/6 | 3 ± 0 |

The table shows that co-immunization of the peptide analogue (91K>A) could specifically inhibit induction of EAE by MBP (87–99), but not inhibit induction of EAE by MBP (68–88), a peptide from a different region. Moreover, the peptide analogue did not cause disease.

EXAMPLE 11

TNF-α Production After Treatment With Peptide Analogues

Cytokine production in draining lymph node cells from rats injected with MBP (87–99) alone or with the peptide analogue (91K>A) was determined. IFN-γ and TNF-α production were measured.

Draining lymph node cells ($10^7$ cells/ml) were stimulated in vitro with different concentrations of MBP (87–99) or peptide analogue. Supernatants were collected after 24 and 48 hours. IFN-γ was determined after 48 hours by use of a rat IFN-γ ELISA kit (GIBCO BRL). TNF-α was measured after 24 hours by ELISA kit (Genzyme Corp., Cambridge, Mass.).

Figure 7A:
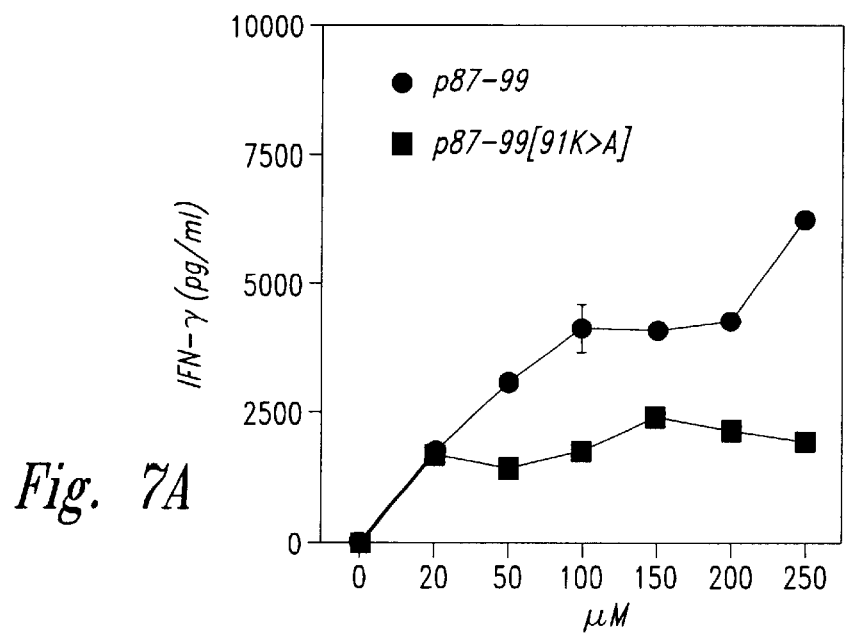
FIGS. 7A and 7B are a pair of graphs showing the amount of IFN-γ and TNF-α production from draining lymph node cells (DLNC). DLNC were stimulated with MBP (87–99) alone (●) or with the peptide analogue (91K>A) (■).
Figure 7B:
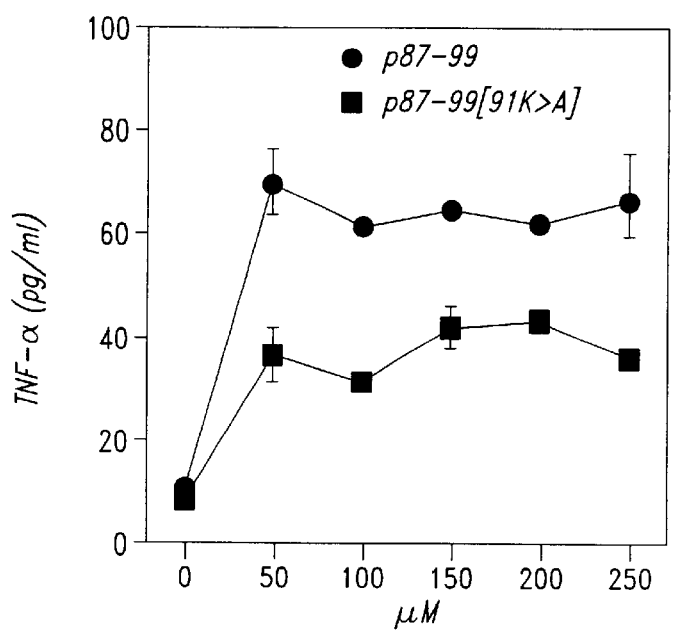

As can be seen in FIG. 7, the peptide analogue caused a marked decrease in cytokine production at all doses greater than 20 μM for TNF-α and at all doses for IFN-γ.

From the foregoing, it will be evident that although specific embodiments of the invention have been described herein for the purpose of illustrating the invention, various modifications may be made without deviating from the spirit and scope of the invention.

What is claimed is:

1. A peptide analogue comprising amino acid residues 87–99 of human myelin basic protein, wherein lysine at position 91 is altered to another amino acid selected from the group consisting of a D-amino acid, glycine, glutamic acid, phenylalanine, arginine, asparagine, histidine, leucine, and serine.

2. The peptide analogue of claim 1 wherein the amino acid at position 91 is altered to a D-amino acid.

3. The peptide analogue of claim 2 wherein the amino acid at position 91 is altered to D-lysine.

4. The peptide analogue of claim 1 wherein the alteration at position 91 results in reduced expression of TNF-α from MBP-reactive T cells upon contacting the MBP-reactive T cells with the peptide analogue.

5. A pharmaceutical composition comprising a peptide analogue of amino acid residues 87–99 of human myelin basic protein, wherein the amino acid at position 91 is altered to D-lysine.

6. A method of treating multiple sclerosis, comprising administering to a patient a therapeutically effective amount of a pharmaceutical composition comprising a peptide analogue comprising amino acid residues 87–99 of myelin basic protein, wherein the L-lysine residue at position 91 is replaced by another amino acid, in combination with a physiologically acceptable carrier or diluent and wherein said peptide analogue is not administered in the form of a noncovalent complex with a Major Histocompatibility Complex (MHC) component.

7. The method of claim 6, wherein the amino acid at position 91 is altered with an amino acid selected from the group consisting of D-lysine, alanine, glycine, glutamic acid, phenylalanine, arginine, asparagine, histidine, leucine and serine.

8. The method of claim 6, wherein the amino acid at position 91 is altered to a non-conservative amino acid.

9. The method of claim 6, wherein the amino acid at position 91 is altered to D-lysine.

10. The method of claim 6, wherein the alteration at position 91 results in reduced expression of TNF-$\alpha$ from MBP-reactive T cells upon contacting the MBP-reactive T cells with the peptide analogue.

* * * * *

UNITED STATES PATENT AND TRADEMARK OFFICE
CERTIFICATE OF CORRECTION

PATENT NO. : 6,369,033 B1
DATED : April 9, 2002
INVENTOR(S) : Lawrence Steinman et al.

It is certified that error appears in the above-identified patent and that said Letters Patent is hereby corrected as shown below:

Column 14,
Line 19, "for TNF-α and at all doses for IFN-γ." should read as -- for IFN-γ and at all doses for TNF-α. --.

Signed and Sealed this

Twenty-second Day of November, 2005

JON W. DUDAS
*Director of the United States Patent and Trademark Office*